(12) United States Patent
Ponder

(10) Patent No.: US 7,297,801 B2
(45) Date of Patent: Nov. 20, 2007

(54) PROCESS FOR THE PRODUCTION OF 2-OXA-3-ONE ANDROSTANE DERIVATIVES

(75) Inventor: Garratt W. Ponder, Alpharetta, GA (US)

(73) Assignee: Barr Laboratories, Inc., Woodcliff Lake, NJ (US)

( * ) Notice: Subject to any disclaimer, the term of this patent is extended or adjusted under 35 U.S.C. 154(b) by 695 days.

(21) Appl. No.: 10/779,519

(22) Filed: Feb. 13, 2004

(65) Prior Publication Data

US 2004/0230062 A1    Nov. 18, 2004

Related U.S. Application Data

(60) Provisional application No. 60/447,457, filed on Feb. 14, 2003.

(51) Int. Cl.
*C07D 311/94* (2006.01)
(52) U.S. Cl. .................................................. 549/383
(58) Field of Classification Search ................ 549/383
See application file for complete search history.

(56) References Cited

U.S. PATENT DOCUMENTS

| 3,128,283 A | 4/1964 | Pappo |
| 6,583,298 B1 | 6/2003 | Santa et al. |
| 2003/0032817 A1* | 2/2003 | Cabaj et al. |

OTHER PUBLICATIONS

Koizumi et al., "Antiandrogen, IV. C-17 spiro 2-oxasteroids.", Chem. Pharm. Bull., vol. 44(11), pp. 2162-2164, 1996.*
Rasmusson et al., "Azasteroids as inhibitors of rat prostatic 5alpha-reductase." J. Med. Chem., vol. 27, pp. 16901701, 1984.*

* cited by examiner

*Primary Examiner*—Barbara P. Badio
(74) *Attorney, Agent, or Firm*—Hutchison Law Group PLLC

(57) ABSTRACT

The present invention relates to processes for the production of 2-oxa-3-one androstane derivatives. The processes comprise reacting a 3-one androstane derivative with ozone to form a 2-oxa-3-one androstane derivative.

20 Claims, No Drawings

PROCESS FOR THE PRODUCTION OF 2-OXA-3-ONE ANDROSTANE DERIVATIVES

CROSS REFERENCE TO RELATED APPLICATIONS

This application claims the benefit of U.S. Provisional Application No. 60/447,457, filed Feb. 14, 2003, the entire content of which is incorporated herein by reference.

FIELD OF THE INVENTION

The present invention generally relates to methods of producing 2-oxa-3-one androstane derivatives.

BACKGROUND OF THE INVENTION

Methods of producing 2-oxa-3-one androstane derivatives such as oxandrolone (i.e., 17β-hydroxy-17α-methyl-2-oxa-5α-androstan-3-one) are known. For example, U.S. Pat. No. 6,583,298 describes a process for the synthesis of 17β-hydroxy-17α-methyl-2-oxa-5α-androstane-3-one, U.S. patent application Publication No. 2003/0032817 describes a process for the synthesis of oxandrolone, and U.S. Patent No. 3,128,283 describes 17-oxygenated oxa-steroids and intermediates thereto. However, as 2-oxa-3-one androstane derivatives such as oxandrolone have various therapeutic uses, improved methods for producing 2-oxa-3-one androstane derivatives are desirable.

SUMMARY OF THE INVENTION

The methods of the present invention relate to producing 2-oxa-3-one androstane derivatives from 3-one androstane derivatives. In one aspect, a process is provided for the production of a 2-oxa-3-one androstane derivative comprising reacting a 3-one androstane derivative with ozone to form a 2-oxa-3-one androstane derivative.

In another aspect of the invention, a process is provided for the production of oxandrolone comprising reacting mestanolone with ozone to form oxandrolone.

In yet another aspect, a process is provided for the production of oxandrolone comprising reacting mestanolone with ozone in the presence of hydrogen peroxide in a temperature range from about 1° C. to about 50° C. for about 3 hours to about 5 hours with the ozone being present in a mixture of oxygen and ozone.

In a further aspect, a process for the production of a 2-oxa-3-one androstane derivative is provided comprising reacting a 3-one androstane derivative of formula (IV)

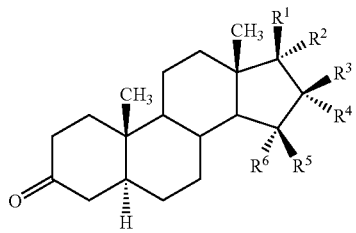

(IV)

with ozone to form a 2-oxa-3-one androstane derivative of formula (V)

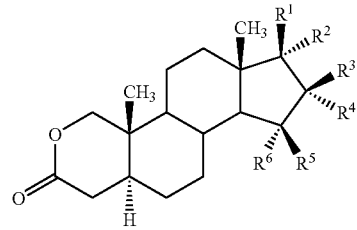

(V)

wherein $R^1$, $R^2$, $R^3$, $R^4$, $R^5$, and $R^6$ are independently selected from the following group: hydrogen, $C_{1-10}$ alkyl, $C_{1-10}$ ketone, phosphate, $C_{1-10}$ alkyl carboxylate, amino, hydroxy, thiol, $C_{1-10}$ thioalkyl, $C_{1-10}$ alkoxy, substituted $C_{1-10}$ alkyl, and halogen.

DESCRIPTION OF THE INVENTION

The present invention relates to methods of producing 2-oxa-3-one androstane derivatives from 3-one androstane derivatives using ozone.

Definitions

Unless otherwise stated, the following terms used herein will have the meanings given below:

"Alkyl" means a branched or unbranched saturated hydrocarbon radical preferably having from 1 to 20 carbon atoms.

"$C_{1-10}$ alkyl" means an alkyl group having from 1 to 10 carbon atoms.

"Ketone" means the group —(C)O(alkyl).

"$C_{1-10}$ ketone" means the group —(C)O($C_{1-10}$ alkyl).

"Phosphate" means the group —O(P)O(OH)$_2$.

"Alkyl carboxylate" means the group —(C)OO-(alkyl).

"$C_{1-10}$ alkyl carboxylate" means the group —(C)OO—($C_{1-10}$ alkyl).

"Amino" means the group —N(R)$_2$, wherein each R is independently selected from hydrogen, alkyl, and substituted alkyl, and preferably is independently selected from hydrogen, $C_{1-10}$ alkyl, and substituted $C_{1-10}$ alkyl.

"Hydroxy" means the group —OH.

"Thiol" means the group —SH.

"Thioalkyl" means the group —S-alkyl.

"$C_{1-10}$ thioalkyl" means the group —S—($C_{1-10}$ alkyl).

"Alkoxy" means the group —O-alkyl.

"$C_{1-10}$ alkoxy" means the group —O—($C_{1-10}$ alkyl).

"Halogen" means chlorine (Cl), bromine (Br), iodine (I), or fluorine (F).

"Substituted alkyl" means an alkyl group in which one or more of the hydrogens are independently replaced with an atom or group such as, for example, a ketone, a phosphate, an alkyl carboxylate, an amino, a hydroxy, a thiol, a thioalkyl, an alkoxy, a halogen, or any other atom or group that may be substituted for a hydrogen in an alkyl group.

"Substituted $C_{1-10}$ alkyl" means a $C_{1-10}$ alkyl group in which one or more of the hydrogens are independently replaced with a substituent selected from the following group: $C_{1-10}$ ketone, phosphate, $C_{1-10}$ alkyl carboxylate, amino, hydroxy, thiol, $C_{1-10}$ thioalkyl, $C_{1-10}$ alkoxy, and halogen.

"Androstane derivative" means a steroid having one or more changes to the steroid structure of formula (I) shown below.

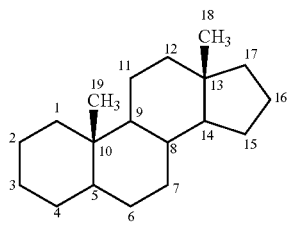

(I)

The one or more changes may be one atom substituted for a carbon (e.g., an oxygen substituted for the carbon at position 2) or may be an atom or group substituted for one or more hydrogens bonded to one of the carbons of the steroid structure (e.g., an oxygen with a double bond (i.e., the group=O) substituted for the two hydrogens bonded to the carbon in position 3). In addition, the one or more changes could be a substitution of a double bond in the place of two hydrogen atoms separately bonded to two different carbon atoms that are bonded to one another (e.g., a double bond could be substituted for a hydrogen atom bonded to the carbon at position 16 and a hydrogen atom at position 17). The one or more changes may include independently replacing one or more of the hydrogen atoms in the steroid structure with an atom or group such as, for example, an alkyl, a ketone, a phosphate, an alkyl carboxylate, an amino, a hydroxy, a thiol, a thioalkyl, an alkoxy, a halogen, a substituted alkyl, or any other atom or group that may be substituted for a hydrogen in the steroid structure of formula (I).

"3-one androstane derivative" means an androstane derivative having an oxygen with a double bond substituted for the two hydrogens bonded to the carbon in position 3 of the steroid. A "3-one androstane derivative" may also have other changes as defined for an androstane derivative. For example, one or more of the carbons at positions 14-17 may have one or both of their hydrogens replaced with a substituent selected from the following group: $C_{1-10}$ alkyl, $C_{1-10}$ ketone, phosphate, $C_{1-10}$ alkyl carboxylate, amino, hydroxy, thiol, $C_{1-10}$ thioalkyl, $C_{1-10}$ alkoxy, substituted $C_{1-10}$ alkyl, and halogen. An example of a "3-one androstane derivative" is mestanolone, shown below as formula (II):

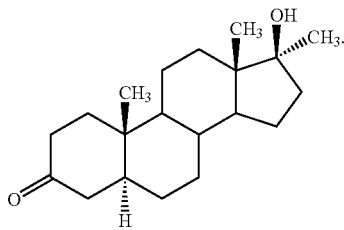

(II)

"2-oxa-3-one androstane derivative" means an androstane derivative having an oxygen atom substituted for the carbon in position 2 of the steroid and having an oxygen with a double bond substituted for the two hydrogens bonded to the carbon in position 3 of the steroid. A "2-oxa-3-one androstane derivative" may also have other changes as defined for an androstane derivative. For example, one or more of the carbons at positions 14-17 may have one or both of their hydrogens replaced with a substituent selected from the following group: $C_{1-10}$ alkyl, $C_{1-10}$ ketone, phosphate, $C_{1-10}$ alkyl carboxylate, amino, hydroxy, thiol, $C_{1-10}$ thioalkyl, $C_{1-10}$ alkoxy, substituted $C_{1-10}$ alkyl, and halogen. An example of a "2-oxa-3-one androstane derivative" is oxandrolone, shown below as formula (III):

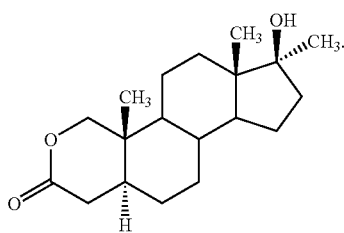

(III)

According to the present invention, a 2-oxa-3-one androstane derivative is produced by reacting a 3-one androstane derivative with ozone. The 3-one androstane derivative may be in solution, and is preferably in an aqueous solution. The ozone that is reacted with the 3-one androstane derivative is preferably present in a mixture of ozone and oxygen. In one embodiment, the reaction is conducted by bubbling a mixture of ozone and oxygen through an aqueous solution of a 3-one androstane derivative. The reaction is preferably performed in an explosion-proof vessel, although other reaction vessels could also be used to carry out the reaction.

The reaction of the 3-one androstane derivative with ozone is preferably conducted in the presence of a peroxide. The peroxide may be an organic peroxide or an inorganic peroxide. One preferred inorganic peroxide is hydrogen peroxide ($H_2O_2$).

In one embodiment, the 3-one androstane derivative may be in an aqueous solution and a peroxide (e.g., hydrogen peroxide) may be continuously added (e.g., by dropwise addition to the solution) such that the peroxide is present during the entire reaction period or a portion of the reaction period.

The reaction of a 3-one androstane derivative with ozone may be carried out over varying periods of time such as, for example, 1-24 hours, preferably 2-12 hours, more preferably 3-5 hours. The reaction of a 3-one androstane derivative with ozone may also be carried out in varying ranges of temperatures such as, for example, in a temperature range between about 1° C. to about 50° C., preferably in a temperature range between about 5° C. to about 40° C., more preferably in a temperature range between about 10° C. to about 30° C.

After performing the reaction, the reaction mixture containing the 2-oxa-3-one androstane derivative may be isolated and/or purified according to known procedures. For example, when the reaction is performed using an aqueous solution of a 3-one androstane derivative, an organic solvent (e.g., methylene chloride) may be used to perform an extraction. If such an extraction is performed, the reaction solution may be diluted with water if desired. In addition, the reaction vessel and/or reaction mixture may be allowed to return to room temperature (if not already at room temperature) before isolating and/or purifying the 2-oxa-3-one androstane derivative.

In one aspect, the 3-one androstane derivative is mestanolone (Formula (II) below), which is reacted with ozone to produce oxandrolone (Formula (III) below) as shown by the following reaction scheme:

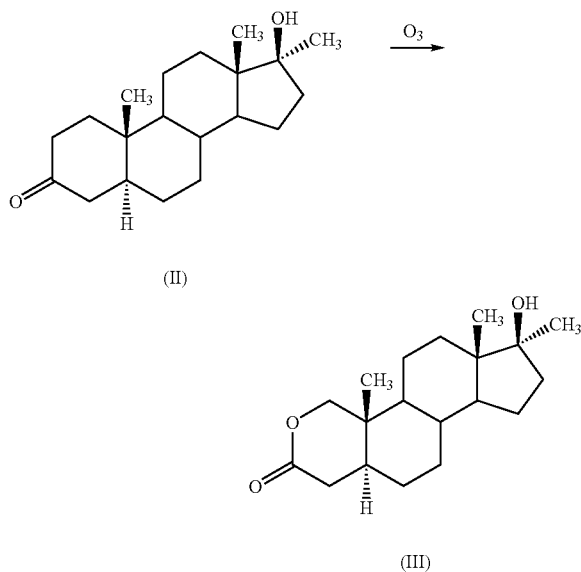

The mestanolone (Formula (II)) is preferably in aqueous solution and the ozone is preferably present as a mixture of ozone and oxygen. The reaction is preferably performed by bubbling the ozone/oxygen mixture through the aqueous solution of mestanolone. In addition, a peroxide (e.g., hydrogen peroxide) is preferably added continuously to the reaction solution (e.g., by dropwise addition) while performing the reaction.

In another aspect, a 3-one androstane derivative of formula (IV) is reacted with ozone to produce a 2-oxa-3-one androstane derivative of formula (V) according to the following reaction scheme:

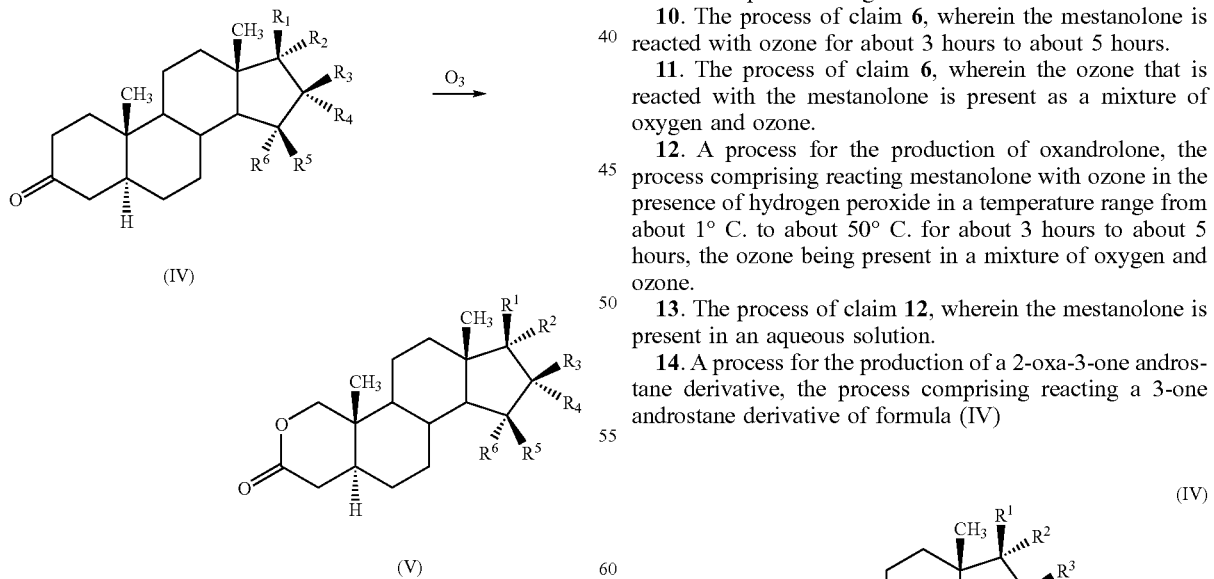

wherein $R^1$, $R^2$, $R^3$, $R^4$, $R^5$, and $R^6$ are independently selected from the following group: hydrogen, $C_{1-10}$ alkyl, $C_{1-10}$ ketone, phosphate, $C_{1-10}$ alkyl carboxylate, amino, hydroxy, thiol, $C_{1-10}$ thioalkyl, $C_{1-10}$ alkoxy, substituted $C_{1-10}$ alkyl, and halogen.

The 3-one androstane derivative of formula (IV) is preferably in aqueous solution and the ozone is preferably present as a mixture of ozone and oxygen. The reaction is preferably performed by bubbling the ozone/oxygen mixture through the aqueous solution of the 3-one androstane derivative of formula (IV). In addition, a peroxide (e.g., hydrogen peroxide) is preferably added continuously to the reaction solution (e.g., by dropwise addition) while performing the reaction.

While the invention has been described in detail and with reference to specific embodiments thereof, it will be apparent to one skilled in the art that various changes and modifications can be made without departing from the spirit and scope of the invention.

What is claimed is:

1. A process for the production of a 2-oxa-3-one androstane derivative, the process comprising reacting a 3-one androstane derivative with ozone to form a 2-oxa-3-one androstane derivative, wherein the reaction is conducted in the presence of an organic or inorganic peroxide.

2. The process of claim 1, wherein the peroxide is hydrogen peroxide.

3. The process of claim 1, wherein the reaction is carried out in a temperature range from about 1° C. to about 50° C.

4. The process of claim 1, wherein the 3-one androstane derivative is reacted with ozone for about 3 hours to about 5 hours.

5. The process of claim 1, wherein the ozone that is reacted with the 3-one androstane derivative is present as a mixture of oxygen and ozone.

6. A process for the production of oxandrolone, the process comprising reacting mestanolone with ozone to form oxandrolone.

7. The process of claim 6, wherein the reaction is conducted in the presence of an organic or inorganic peroxide.

8. The process of claim 7, wherein the peroxide is hydrogen peroxide.

9. The process of claim 6, wherein the reaction is carried out in a temperature range from about 1° C. to about 50° C.

10. The process of claim 6, wherein the mestanolone is reacted with ozone for about 3 hours to about 5 hours.

11. The process of claim 6, wherein the ozone that is reacted with the mestanolone is present as a mixture of oxygen and ozone.

12. A process for the production of oxandrolone, the process comprising reacting mestanolone with ozone in the presence of hydrogen peroxide in a temperature range from about 1° C. to about 50° C. for about 3 hours to about 5 hours, the ozone being present in a mixture of oxygen and ozone.

13. The process of claim 12, wherein the mestanolone is present in an aqueous solution.

14. A process for the production of a 2-oxa-3-one androstane derivative, the process comprising reacting a 3-one androstane derivative of formula (IV)

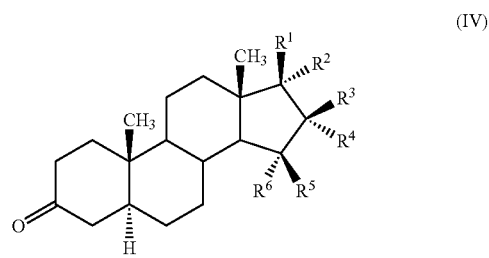

wherein $R^1$, $R^2$, $R^3$, $R^4$, $R^5$, and $R^6$ are independently selected from the following group: hydrogen, $C_{1-10}$ alkyl, $C_{1-10}$ ketone, phosphate, $C_{1-10}$ alkyl carboxylate, amino, hydroxy, thiol, $C_{1-10}$ thioalkyl, $C_{1-10}$ alkoxy, substituted $C_{1-10}$ alkyl, and halogen; with ozone to form a 2-oxa-3-one androstane derivative of formula (V)

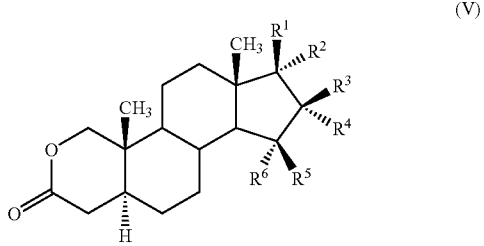

(V)

wherein $R^1$, $R^2$, $R^3$, $R^4$, $R^5$, and $R^6$ are as above in formula (IV).

15. The process of claim 14, wherein the reaction is conducted in the presence of an organic or inorganic peroxide.

16. The process of claim 15, wherein the peroxide is hydrogen peroxide.

17. The process of claim 14, wherein the reaction is carried out in a temperature range from about 1° C. to about 50° C.

18. The process of claim 14, wherein the 3-one androstane derivative of formula (IV) is reacted with ozone for about 3 hours to about 5 hours.

19. The process of claim 14, wherein the ozone that is reacted with the 3-one androstane derivative of formula (IV) is present as a mixture of oxygen and ozone.

20. The process of claim 19, wherein the reaction is conducted in the presence of hydrogen peroxide.

* * * * *